(12) United States Patent
Michaelian

(10) Patent No.: US 7,833,014 B2
(45) Date of Patent: Nov. 16, 2010

(54) DENTAL DEVICE AND METHOD OF USE

(76) Inventor: Andre Michaelian, 3150 N. Tenaya, Suite #200, Las Vegas, NV (US) 89128

( * ) Notice: Subject to any disclaimer, the term of this patent is extended or adjusted under 35 U.S.C. 154(b) by 0 days.

(21) Appl. No.: 12/147,224

(22) Filed: Jun. 26, 2008

(65) Prior Publication Data
US 2008/0261171 A1 Oct. 23, 2008

Related U.S. Application Data

(62) Division of application No. 11/013,673, filed on Dec. 15, 2004, now abandoned.

(51) Int. Cl.
*A61C 3/06* (2006.01)
(52) U.S. Cl. .................... 433/125; 433/83; 433/112
(58) Field of Classification Search ................ 433/82, 433/83, 85, 87, 89, 91, 96, 112, 122, 124, 433/125, 127, 133; 222/64, 65, 104–106, 222/167–172, 206, 210, 211, 214, 215; 401/148, 401/153, 272
See application file for complete search history.

(56) References Cited

U.S. PATENT DOCUMENTS

| | | | | |
|---|---|---|---|---|
| 1,959,365 | A * | 5/1934 | Jeffreys | 222/104 |
| 2,080,134 | A * | 5/1937 | Jezler | 222/104 |
| 2,218,290 | A * | 10/1940 | Moricich | 222/104 |
| 3,157,061 | A | 11/1964 | Parker | |
| 3,389,468 | A * | 6/1968 | Lewis et al. | 433/80 |
| 3,409,224 | A | 11/1968 | Harp | |
| 3,472,045 | A | 10/1969 | Nelsen | |
| 3,579,835 | A | 5/1971 | Levenson | |
| 3,870,198 | A * | 3/1975 | Cohen | 222/104 |
| 4,266,933 | A | 5/1981 | Warden et al. | |
| 4,277,194 | A * | 7/1981 | Smith | 401/173 |
| 4,332,497 | A * | 6/1982 | Rodriguez | 401/154 |
| 4,417,874 | A | 11/1983 | Andersson et al. | |
| 5,334,020 | A | 8/1994 | Eckert | |
| 5,692,901 | A | 12/1997 | Roth et al. | |
| 5,871,353 | A | 2/1999 | Pierce et al. | |
| 5,902,107 | A | 5/1999 | Lowell | |
| 5,913,314 | A * | 6/1999 | Garrett | 132/112 |
| 6,053,732 | A | 4/2000 | Sale | |
| 6,099,309 | A | 8/2000 | Cardarelli | |

(Continued)

FOREIGN PATENT DOCUMENTS

GB 1 215 765 A 12/1970

*Primary Examiner*—Cris L Rodriguez
*Assistant Examiner*—Michael R Ballinger
(74) *Attorney, Agent, or Firm*—Greenberg Traurig

(57) ABSTRACT

A prophy device incorporating a shaft and one or more corrugated members which eliminate the need for plastic gears of the prior art is disclosed. The corrugated members effectively transfer rotational energy from a shaft to an applicator. In another version, a flexible paste chamber contains polish within a housing of the device. A difference between a rotational speed at a front of the paste chamber and rear of the paste chamber causes the flexible chamber to contract on itself thereby automatically forcing polish from the chamber and into a polish applicator. A user dictates the amount of polish dispensed by controlling the rotational speed at the front of the paste chamber by pressing the polish applicator against the teeth of a patient. As the speed differential increases, the amount of polish dispensed increases as well.

18 Claims, 4 Drawing Sheets

U.S. PATENT DOCUMENTS

| | | |
|---|---|---|
| 6,241,412 B1 * | 6/2001 | Spies et al. ................. 401/129 |
| 6,257,886 B1 | 7/2001 | Warner |
| 6,632,090 B1 | 10/2003 | Randolph |
| 2004/0014004 A1 | 1/2004 | Garrison et al. |
| 2004/0240928 A1 * | 12/2004 | Trocino ..................... 401/277 |

* cited by examiner

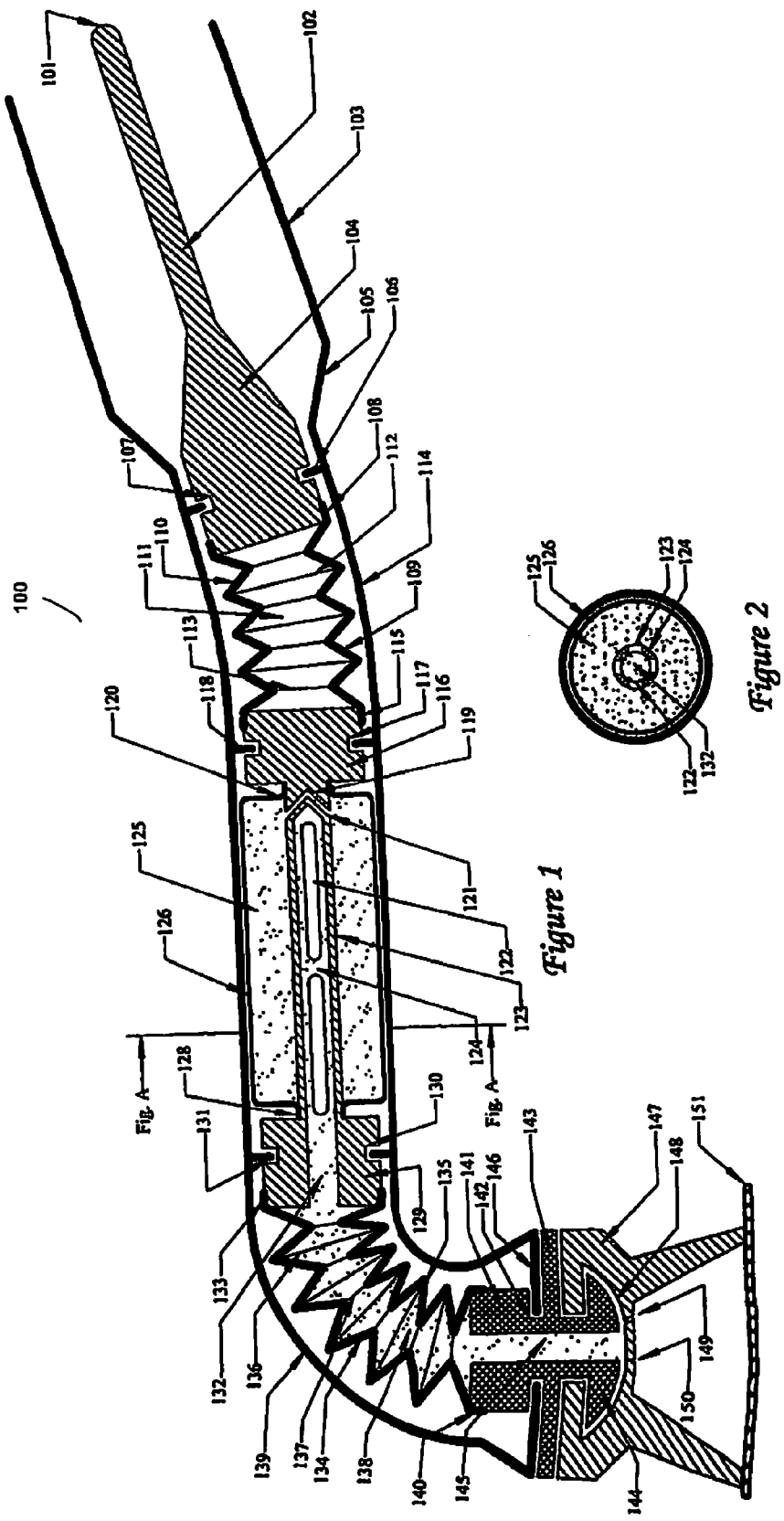

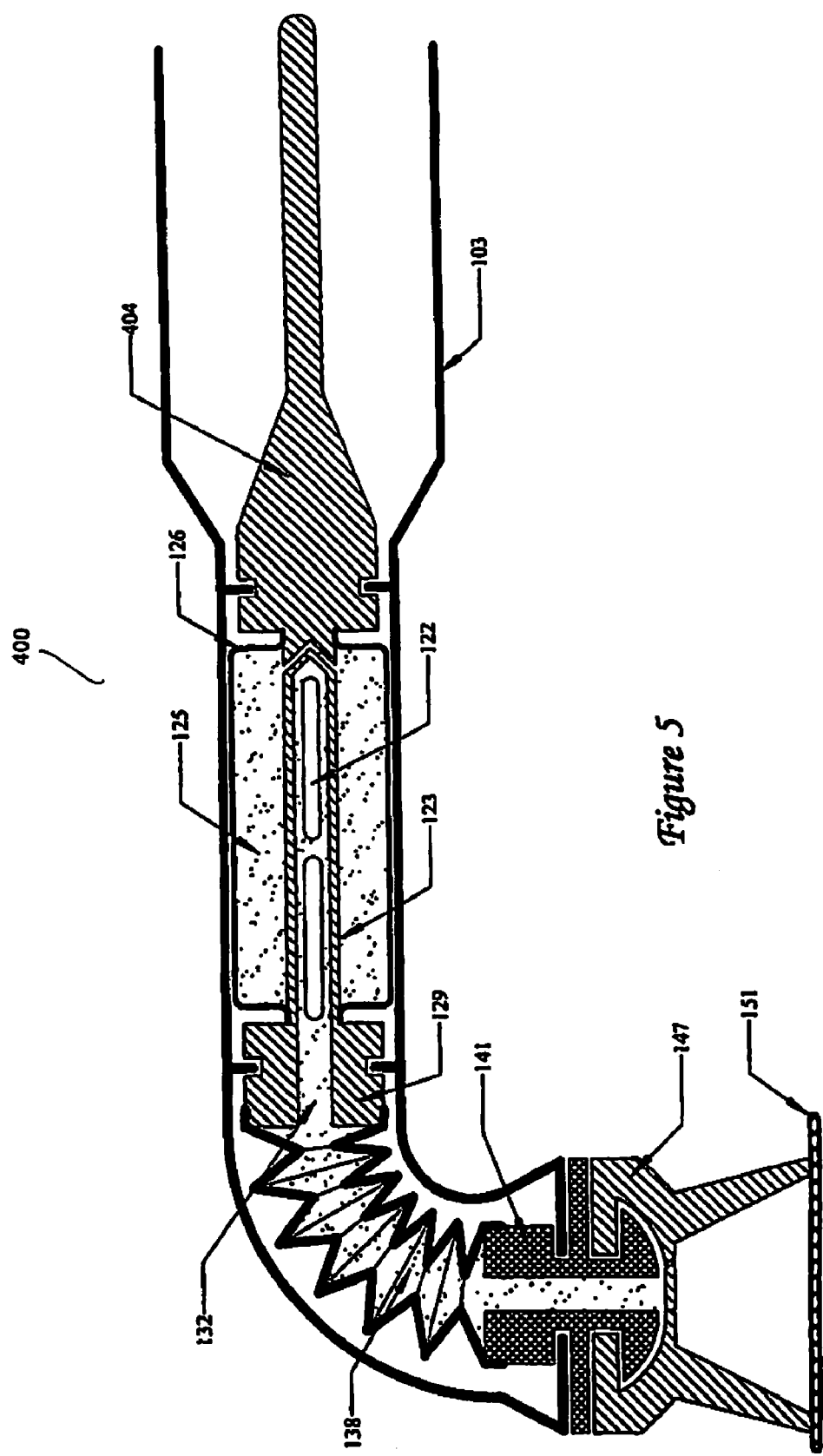

DENTAL DEVICE AND METHOD OF USE

CROSS REFERENCE TO RELATED APPLICATIONS

This application is a divisional of U.S. application Ser. No. 11/013,673 filed Dec. 15, 2004 now abandoned.

FIELD OF THE INVENTION

The embodiments of the present invention relate to dentistry. More particularly, the embodiments relate to a simple and inexpensive disposable tool for polishing teeth and automatically dispensing polishing paste.

BACKGROUND

Maintaining clean teeth is integral to having healthy oral environment. Accordingly, a myriad of products and dental services are available to clean teeth. More specifically, dental professionals offer cleaning and polishing services. Moreover, most experts recommend such services once or twice a year.

While the process of cleaning teeth utilizes one or more rigid tools for prying tarter and related build-up from the teeth, polishing paste is applied using an air or electric driven prophy device. Prophy devices conventionally communicate with an air or electric source which is driven by a motor. The prophy device may be disposable or may be sterilized after each polishing. In either case, the prophy device includes a polish applicator fabricated of a pliable material, such as rubber. In practice, a portion of polishing paste is manually placed in a small cup of the applicator. The applicator is then rotatably driven and placed in contact with the teeth to be polished. During a standard polishing, the polishing cup must be intermittently filled with polishing paste. Unfortunately, each filling of the polishing cup requires the dentist or hygienist to stop the polishing process. Thus, because of the numerous breaks, the time for polishing is unnecessarily extended.

In addition to wasting time, the refilling of the prophy cup requires the dentist to remove the instrument from the patient's mouth and refill the cup. This repeated removal of the instrument increases the risk of transferring a patient's saliva, food debris, or plaque and potential associated blood-borne pathogens.

Another disadvantage is that gears inside the current prophy devices tend to fail when used at high speed and/or for long durations. The failure increases both time and cost.

The patent literature is replete with apparatuses and devices integrating a source of polishing paste with the actual applicator. Accordingly, the dentist is not required to stop the polishing process to re-fill the cup. Nonetheless, each of the prior apparatuses and devices are impractical, complex and overly costly in relation to the conventional models discussed above. Thus, even though patented designs exist, they are not available in the market because of the noted shortcomings.

Conventional polishing devices also incorporate a system of plastic gears designed to rotate the polishing applicator. More specifically, a first plastic shaft attached at one end to a drive device extends an internal length of the prophy device where a gear resides at a second end of the shaft. A second shaft has a gear at a first end such that it meshes with the gear at the second end of the first shaft. The second shaft extends at an approximately 90° angle from the first shaft and is fixed at a second end to the polish applicator. Consequently, driving or rotating the first shaft causes the first shaft gear to transfer power (i.e., rotational energy) to the second gear which then drives or rotates the polish applicator for application of polish to the teeth. Unfortunately, the plastic gears tend to fail during use thereby requiring the operator to replace the prophy device. Not only is time wasted, but the cost to the care provider and patient increases.

Thus, there continues to be the need for a simple, inexpensive polishing device capable of automatically dispensing polish. In addition, the polishing device should eliminate the plastic gears which can fail when in operation.

SUMMARY

Accordingly, a first embodiment of the present invention comprises a disposable prophy device which contains and dispenses polishing paste. The paste is contained in a flexible paste chamber within a prophy housing. The unique design of the prophy angle allows the user to operate the prophy device at any speed without paste being dispensed as long as a prophy cup does not experience any resistance such as that created during contact with a tooth. As the prophy cup contacts a tooth, the resistance experienced by the cup is transferred to the paste chamber such that the paste chamber tends to contract around itself causing paste to be forced from the paste chamber and into the prophy cup. As more pressure is applied on the tooth, more paste is dispensed and when pressure is reduced, less of the paste is dispensed into the prophy cup. Therefore, the new prophy angle design delivers paste on demand in response to the level of pressure placed on the tooth by the prophy cup. It is common practice for the operator of a prophy angle to exert greater pressure on teeth that have significant plaque buildup than on teeth with little plaque buildup.

In addition, the use of corrugated sections in combination with rigid shafts and disk members eliminates the gears of the prior art and provides for an ergonomic design. Even through there exists one or more bends in a housing of the prophy angle, the corrugated sections transfer rotational energy from a rotating shaft to a prophy cup without any gears.

During use a professional user (e.g., dental hygienist) removes an individually packaged prophy angle and inserts the drive end of the prophy device into the nose cone of a dental hand piece and when ready to use, a seal on the prophy cup is peeled off and the procedure may begin. Herein, throughout the description of the embodiments of present invention, numerous references are made to paste. It should be understood that paste is intended to be construed broadly to cover any prophylaxis medium or dentifrice, such as paste or gel. In fact, the device herein is not limited to the dental industry and may facilitate non-dental applications of any type of paste, gel or materials having similar properties.

Other features, embodiments and variations will become evident from the following detailed description, drawings and claims.

BRIEF DESCRIPTION OF THE DRAWINGS

FIG. 1 shows an internal view of a first embodiment of the present invention;

FIG. 2 shows a cross-sectional view along direction A of FIG. 1;

FIG. 5 shows an internal view of a fourth embodiment of the present invention.

DETAILED DESCRIPTION

Figure 3:
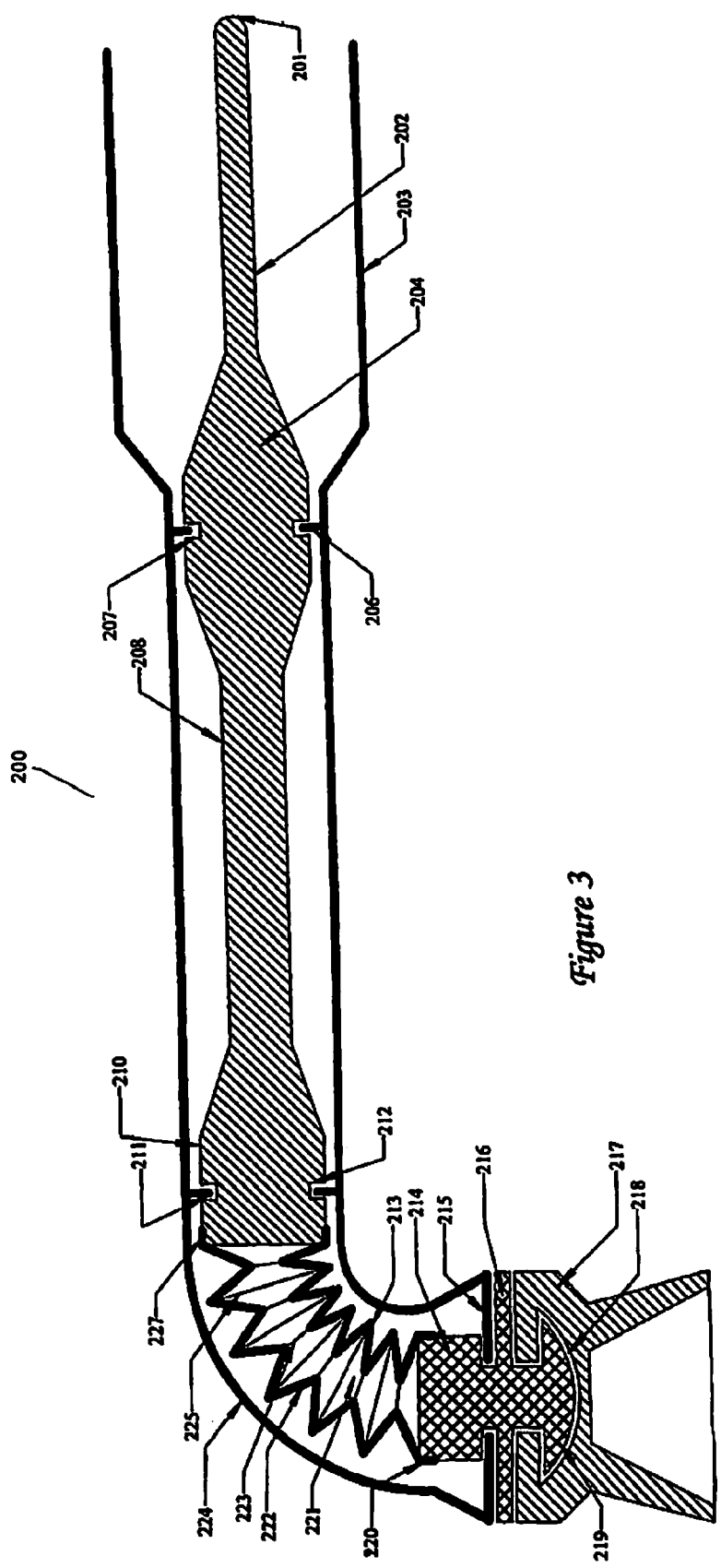
FIG. 3 shows an internal view of a second embodiment of the present invention.

A disposable conventional prophy device is joined to an air or electric source and motor (i.e., hand piece motor) which drive a first shaft. The air or electric source is controlled by an operator through hand or feet movements. The first shaft then drives a second shaft via a pair of meshed gears. Then, the second shaft drives a polish applicator. As disclosed below, the embodiments of the present invention eliminate the need for gears and the repetitive manual application of polish into the prophy cup.

Reference is now made to the figures wherein like parts are referred to by like numerals throughout. FIG. 1 shows a prophy device generally referred to by reference numeral 100. In a conventional manner, the prophy device 100 is received by a hand piece motor handle (not shown). A main housing 105 comprises a circular cross section, which incorporates a first bend 114, a second bend 139, a first open end 103 and a second open end 146. Within the main housing 105, there are multiple protrusions 106, 118, 131, and 146 which act to maintain certain inner components in fixed positions while allowing the inner components to rotate about their longitudinal axes. The first open end 103 is sized to accept a standard nose cone of a dental hand piece motor and the second open end 146 accommodates placement of a prophy cup 147. In combination, the two bends 114, 139 provide an ergonomically designed device 100 for the user and also permit a wider range of access inside a patient's mouth.

The main housing 105 can be manufactured with different materials having different colors, textures and/or dimensions. It should be understood that the embodiments of the present invention are not intended to be limited to prophy paste and should be hereby construed to cover the application of any liquids, gels, pastes or similar materials.

A drive shaft 104 has a first rounded end 101 received by a nose cone of a hand piece motor and a second end 108 attached to a first corrugated drive 111. The hand piece motor maintains connection with the slender shaft 102 by means of a friction grip and transfers rotational energy from the hand piece motor to the drive shaft 104. The circular drive shaft 104 includes a slender shaft 102, widened body 104 and circular notch 107. The circular notch 107 receives protrusion 106 for maintaining the drive shaft 104 in place with respect to the main housing 105 and allowing free rotation of the drive shaft 104 about its longitudinal axis. The second end 108 of the drive shaft 104 is attached to the first corrugated drive 111 such that all the rotational energy generated by the hand piece motor is directly transferred to the first corrugated drive 111.

The first corrugated drive 111 is a hollow multi-fold member which transfers the rotational energy of the drive shaft 104 to a middle drive disk 116. The first corrugated drive 111 also facilitates transfer of the rotational energy through the first bend 114 of the main housing 105 between the drive shaft 104 and the middle drive disk 116. As the first corrugated dive 111 rotates about its longitudinal axis it forces the corrugated segments to contract on one side 110 and expand on the opposite side 109. This change in shape during rotation is possible because of the flexibility of the material used, the hollow nature of the design and the alternating wide 112 and narrow 113 circumferences forming the drive 111. By using this type of corrugated drive 111, the need for the gears of the prior art are eliminated. Prior art gear systems can fail and generate significant noise levels during use. Because of the unique design and function of the first corrugated drive 111 as described herein, the bend 114 between the axis of the drive shaft 104 and the axis of the middle drive disk 116 can be altered per final design requirements.

The circular middle drive disk 116 is attached to the first corrugated drive 111 at a first end 115 and a paste chamber 126 at a second end 120. The paste chamber 126 is fabricated a flexible material. The middle drive disk 116 also has a circular notch 117 which receives protrusion 118 for maintaining the middle drive disk 116 in place with respect to the main housing 105 and allowing free rotation of the middle drive disk 116 about its longitudinal axis. A concave portion 119 of the middle drive disk 116 extending into the paste chamber 126 accommodates a pointed end 121 of central rod 123. This accommodation permits the central rod 123 to rotate independently about its longitudinal axis while being prevented from diverging too substantially from a suitable position with respect to the middle drive disk 116.

The paste chamber 126 functions like a flexible reservoir wherein paste is stored and dispensed on demand during use. The paste chamber 126 attaches at a first end 120 to the middle drive disk 116 and a second end 128 to drive disk 129 which is hollow in the center. Consequently, the rotational energy of the middle drive disk 116 is transferred to the drive disk 129 by the paste chamber 126 only. As long as there is no resistance placed on the drive disk 129, the paste chamber 126 is able to transfer the same rotational energy of the middle drive disk 116 to the drive disk 129 such that both rotate at the same speed. Since the chamber 126 is filled with paste 125, which has mass and occupies a certain volume, it functions like a solid segment. When resistance is placed on the drive disk 129, it creates a speed differential between the drive disk 129 and the middle drive disk 116 causing the paste chamber 126 to compensate for the speed differential by collapsing its flexible walls. As the chamber 126 turns on itself, the volume of the chamber 126 is decreased forcing the paste 125 within the chamber 126 to be pushed out through multiple openings 122 of the central rod 123. The greater the differential speed, the more paste 125 that is pushed out of the chamber 126 through openings 122. When the resistance on the drive disk 129 is removed, no further paste 125 is pushed out.

The circular drive disk 129 is held in place by protrusion 131 which is received by circular notch 130 on the drive disk 129. A first end 128 is attached to the paste chamber 126 and a second end 133 is attached to a second corrugated drive 138. The central rod 123 is an extension of the drive disk 129 with a pointed end 121 accommodated by the middle drive disk 116. The central rod 123 has multiple openings 122 leading to a central channel 132 with one or more rigid support segments 124 for maintaining the shape of the rod 123 during use. As the paste chamber 126 begins collapsing the paste 125 within the chamber 126 is forced to pass through the openings 122 in the rod 123 into the central channel 132 which guides the paste 125 through the drive disk 129. The central rod 123 maintains a fixed distance between the middle drive disk 116 and the drive disk 129 preventing the collapsing paste chamber 126 from pulling the middle drive disks 116 and drive disk 129 toward one another during use. As the paste 125 within the chamber 126 is depleted, the flexible chamber 126 wraps completely around the central rod 123 with no further speed differential compensation.

FIG. 2 shows a cross-sectional view in the direction of A depicted in FIG. 1. The aspects, namely the channel 132, multiple openings 122 and rigid support segments 124, of the rod 123 are clearly visible in FIG. 2. During contraction of the chamber 126, paste 125 is forced from paste chamber 126 through openings 122 and into channel 132 where the paste 125 is forced through drive disk 129.

The second corrugated drive 138 functions like the first corrugated drive 111. The second corrugated drive 138 accepts paste 125 from the central channel 132 which leads through the central rod 123 and the drive disk 129. The second corrugated drive 138 is attached at a first end 133 to the drive disk 129 and at a second end 140 to a prophy cup holder 141. In this manner, the second corrugated drive 138 guides the paste 125 into a channel 145 of the prophy cup holder 141. The second corrugated drive 138 is a hollow multi-fold member which transfers the rotational energy of the drive disk 129 to the prophy cup holder 141. As the second corrugated drive 138 rotates about its curved longitudinal axis, it forces the corrugated segments to contract on one side 135 and expand on an opposite side 134. This change in shape during rotation is possible because of the flexibility of the material used, the hollow nature of the design and the alternating wide 136 and narrow 137 circumferences forming the drive 138. Using this type of corrugated drive 138 transfers rotational energy through bend 139 and eliminates the need for gears as used with prior art prophy designs. Because of the unique design of the second corrugated drive 138, paste 125 is forced and guided through the bend 139.

A circular notch 142 of the prophy cup holder 141 receives protrusion 146 maintaining prophy cup holder 141 in a fixed position during rotation about its longitudinal axis. Since the prophy cup holder 141 is attached to the second corrugated drive 138 which is attached to the drive disk 129, any rotational energy of the drive disk 129 is transferred to a button 144 of the prophy cup holder 141 with no loss in rotational speed. The prophy cup holder 141 defines a central channel 145 which allows paste 125 to be forced and guided from the second corrugated drive 138 into prophy cup 147. Beyond the second open end of the housing 105, the prophy cup holder 141 incorporates a disk segment 143 which maintains the prophy cup holder 141 in place and prevents it from being pulled into the housing 105. Button 144 inserts into the prophy cup 147 to secure the cup 147.

The prophy cup 147 is a separate item which snaps into place on the button 144. The attachment is achieved via the flexible prophy cup 147 having an opening 148 for securely receiving the button 144. To achieve this attachment and prevent paste 125 from exiting therethrough, opening 148 of prophy cup 147 is slightly smaller in size than the receiving button 144 of the prophy cup holder 141. At an inside center of the prophy cup 147 a one way valve opening 149 allows extruding paste 125 to be forced through the prophy cup holder 141 and into the prophy cup 147 where it is used to clean the surface of teeth. The one way valve 149 prevents back flow of paste 125 and/or air from entering and traveling into the paste chamber 126. Ideally, the one way valve 149 is a circular flap which is greater in circumference than the channel 145 of the prophy cup 141. The one way valve 149 rotates about notch 150. Finally, the end of the prophy cup 147 is sealed by a removable film 151 to prevent drying of the paste 125 inside the device. It should be understood that the prophy cup 147 may include other designs and should be hereby construed to include different types of prophy items including prophy brushes and different shaped polishers.

FIG. 3 shows an alternative prophy design 200 without the first bend 114, first corrugated drive 111, middle drive disk 116, paste chamber 126, and drive disk 129. Additionally, prophy cup holder 141 does not contain a central channel. In this alternative design, a shaft 202 extends through a majority of the length of housing 203. A first end 201 of the shaft 202 is for attachment to a hand piece motor and a second end 227 attaches to a corrugated drive 221. The shaft 202 comprises a first expanded portion 204 having notch 207 for receipt of protrusion 206. As with the previous design, the protrusion 206 maintains the shaft 202 in place during rotation along its longitudinal axis. Similarly, and for the same purpose, a second expanded portion 210 has notch 212 for receipt of protrusion 211. Section 208 extends between the first expanded portion 204 and second expanded portion 210.

The corrugated drive 221 is a hollow multi-fold member which transfers the rotational energy of the shaft 202 to the prophy cup holder 214. As the corrugated drive 221 rotates about its curved longitudinal axis, it forces the corrugated segments to contract on one side 213 and expand on an opposite side 222. This change in shape during rotation is possible because of the flexibility of the material used, the hollow nature of the design and the alternating wide 225 and narrow 223 circumferences forming the corrugated drive 221. Using this type of corrugated drive 221 transfers rotational energy through bend 224 and eliminates the need for gears as used with prior art prophy designs.

A second end 220 of the corrugated drive 221 attaches to prophy cup holder 214. A disk 216 beyond the second end 215 of the housing 203 prevents the prophy cup holder 214 from being pulled into the housing 203. Like the embodiment of FIG. 1, a button 219 receives a flexible prophy cup 217. In this embodiment, only the prophy cup 217 contains paste loaded from a separate container by the operator for polishing teeth. For a new patient, a completely new prophy device is attached to the hand piece motor.

Figure 4:
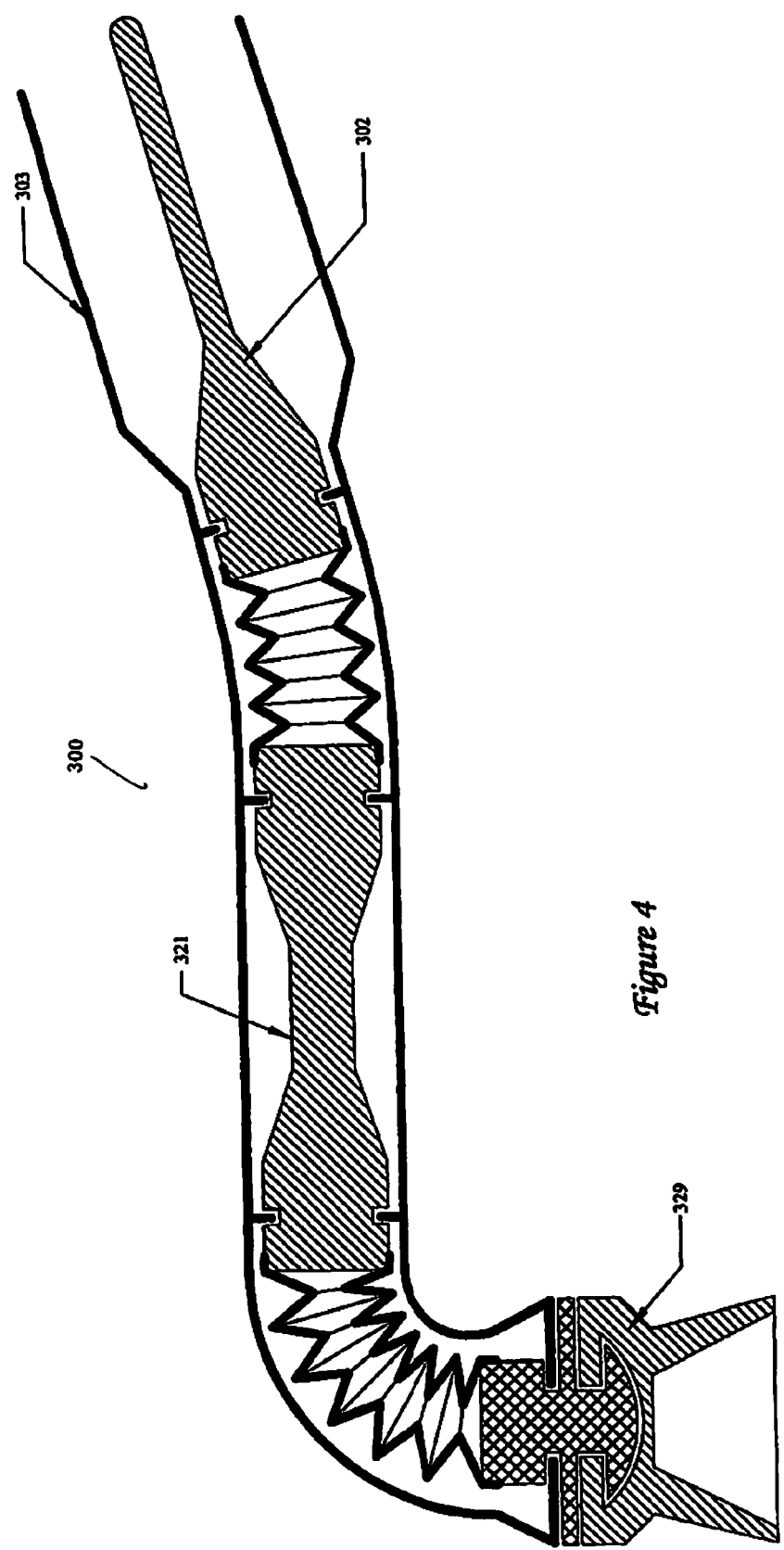
FIG. 4 shows an internal view of a third embodiment of the present invention.

FIG. 4 shows an alternative prophy design 300 without the ability to dispense prophy paste. This embodiment of a prophy device 300 comprising two rigid shafts 302 and 321 within housing 303. Rigid shaft 321 replaces the paste chamber 126 of the embodiment shown in FIG. 1. Like the embodiment shown in FIG. 3, the prophy cup 329 is manually loaded with prophy paste from a separate container by the operator.

FIG. 5 shows a fourth embodiment of a prophy device 400 similar to the embodiment shown in FIG. 1 without first corrugated drive 111, middle drive disk 116 and first bend 114. The first corrugated drive 111 and drive disk 116 is replaced with rigid shaft 404.

The prophy device designs described herein solve the problems, namely complexity, cost of manufacture and failure, associated with the prior art devices. Consequently, the instant designs are able to functionally compete with current commercial models at less cost. Dentists and consumers will both benefit from the unique uncomplicated design.

It should be understood that materials besides dental paste may be applied to items in fields of use unrelated to the dental industry.

Although the invention has been described in detail with reference to several embodiments, additional variations and modifications exist within the scope and spirit of the invention as described and defined in the following claims.

I claim:

1. An application device comprising:
   a housing;
   a rotatable shaft having a first end for attachment to a drive means and a second end attached to a flexible application material chamber;
   a corrugated member attached at a first end to an applicator retaining means and a second end to a disk member, said applicator retaining means including a channel therethrough and configured to receive an applicator; and
   a rod extending from said disk member into said flexible application material chamber, said rod having one or more openings in a surface thereof, said one or more openings accessing an inner channel extending through said rod and disk member, said channel providing a path for material contained within said application material container to exit therefrom wherein the disk member is attached at a first end to said flexible application material chamber and at a second end to said corrugated member; and wherein the device is configured such that rotational energy of the rotatable shaft is transferred to the disk member by the flexible application material chamber only, and when resistance is placed on the disk member, it creates a speed differential between the disk member and the rotatable shaft causing the flexible application material chamber to compensate for the speed differential by collapsing.

2. The application device of claim 1 further comprising an applicator having a rotatable one way flap for providing an opening for application material to be forced into the applicator.

3. The application device of claim 1 wherein the housing contains two or more internal protrusions which are received by corresponding notches in the shaft and disk member.

4. The application device of claim 1 wherein the application material is polishing paste for teeth.

5. The application device of claim 1 wherein the applicator retaining means includes a button for receipt by an opening in an applicator.

6. The application device of claim 1 wherein the corrugated member extends through an acute bend in the housing.

7. The application device of claim 1 wherein the rod extends into the said application material chamber such that a free end of the rod is accommodated by a portion of said rotatable shaft.

8. The application device of claim 7 wherein a position of the free end of the rod is able to fluctuate positions within an area defined by said portion of said rotatable shaft.

9. An application device comprising:

a housing;

a rotatable shaft having a first end for attachment to a drive means and a second end attached to a first corrugated member, said first corrugated member attached to a first disk member, said first disk member attached to a flexible application material container;

a second corrugated member attached to an applicator retaining means, said applicator retaining means including a channel therethrough and configured to receive an applicator; and a second disk member attached at a first end to said flexible application material container and at a second end to said second corrugated member;

a rod extending from said second disk member into said flexible application material container, said rod having one or more openings in a surface thereof, said one or more openings accessing an inner channel extending through said rod and second said disk member, said channel providing a path for material contained within said flexible application material container to exit therefrom;

wherein the device is configured such that the rotational energy of the first disk member is transferred to the second disk member by the flexible application material container only, and when resistance is placed on the second disk member, it creates a speed differential between the first disk member and the second disk member causing the flexible application material container to compensate for the speed differential by collapsing.

10. The application device of claim 9 further comprising an applicator having a rotatable one way flap for providing a passageway for application material to be forced into the applicator.

11. The application device of claim 9 wherein the housing contains three or more internal protrusions which are received by corresponding notches in the shaft, the first disk member and the second disk member.

12. The application device of claim 9 wherein the application material is polishing paste for teeth.

13. The application device of claim 9 wherein the applicator retaining means includes a button for receipt by an opening in the applicator.

14. The application device of claim 9 wherein the first corrugated member extends through an acute bend in the housing.

15. The application device of claim 9 wherein the rod extends into the said flexible application material chamber such that a free end of the rod is accommodated by said first disk member.

16. The application device of claim 15 wherein a position of the free end of the rod is able to fluctuate positions within an area defined by a portion of said first disk member.

17. The application device of claim 9, wherein the rod extends into said flexible application material container such that a rearward end of the rod is accommodated by said first disk.

18. The application device of claim 9 wherein a rearward end of said rod is free to fluctuate positions within a defined area within said application material container.

* * * * *